United States Patent [19]

Fujioka et al.

[11] Patent Number: 4,963,529
[45] Date of Patent: Oct. 16, 1990

[54] STABLE GROWTH HORMONE RELEASING FACTOR PREPARATION

[75] Inventors: Keiji Fujioka, Hyogo; Shigeji Sato; Yoshihiro Takada, both of Osaka, all of Japan

[73] Assignee: Sumitomo Pharmaceuticals Company, Limited, Osaka, Japan

[21] Appl. No.: 168,617

[22] Filed: Mar. 8, 1988

Related U.S. Application Data

[63] Continuation of Ser. No. 813,013, Dec. 24, 1985, abandoned.

[30] Foreign Application Priority Data

Dec. 24, 1984 [JP] Japan .................................. 59-280036
Sep. 18, 1985 [JP] Japan .................................. 60-207244

[51] Int. Cl.$^5$ .............................................. A61K 37/36
[52] U.S. Cl. ......................................... 514/12; 514/21; 514/561; 514/970; 530/324
[58] Field of Search ......................... 424/108; 530/324; 514/12, 21, 970, 561

[56] References Cited

U.S. PATENT DOCUMENTS

| | | | |
|---|---|---|---|
| 3,803,309 | 4/1974 | Desaulles | 424/179 |
| 4,452,775 | 6/1984 | Kent | 514/12 |
| 4,460,576 | 7/1984 | Kawauchi | 514/13 |
| 4,563,352 | 1/1986 | Rivier et al. | 514/12 |
| 4,622,312 | 11/1986 | Felix et al. | 514/12 |

OTHER PUBLICATIONS

Ling et al., PNAS USA, vol. 81 (1984), pp. 4302–4306.
Seifert et al., Nature, vol. 313 (1985), pp. 487–489.

*Primary Examiner*—Jacqueline Stone
*Attorney, Agent, or Firm*—Ladas & Parry

[57] ABSTRACT

Growth hormone releasing factor (GRF) preparation which is excellent in stablity by having human serum albumin or glycine incorporated therein, with or without buffer. An amount of human serum albumin or glycine contained is usually 100 μg to 30 mg per 100 μg GRF. The preparation may be in the solid or solution form, preferably in the lyophilized form. An amount of buffer, if added, is preferably enough so that pH of the preparation is kept at 2–7. More preference is that the preparation is kept in nitrogen gas atmosphere. The lyophilized preparation is readily usable for, for example, injection.

12 Claims, No Drawings

STABLE GROWTH HORMONE RELEASING FACTOR PREPARATION

This is a continuation of co-pending application Ser. No. 813,013, filed on Dec. 24, 1985, now abandoned.

This invention relates to a stable growth hormone releasing factor (hereinbelow abbreviated to GRF) preparation, more precisely, it relates to a GRF preparation containing human serum albumin or glycine as a stabilizer.

GRF is peptide purified and isolated by Guillemin et al from pancrease of a patient with pancreatic tumor showing symptoms of acromegaly. It has the primary structure of amino acids as follows:

H—Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Met—Ser—Arg—Gln—Gln—Gly—Glu—Ser—Asn—Gln—Glu—Arg—Gly—Ala—Arg—Ala—Arg—Leu—NH$_2$ (Guillemin, R., Brazeau, P., Pöhlen, P., Esch, F., Ling, N., & Wehrenberg, W. B.: Growth hormone releasing factor from a human pancreatic tumor that caused acromegaly. Science, 218, 585–587, 1982). It is later identified that it has exactly the same structure as GRF purified from the hypothalamus, and a name of somatocrinin in place of GRF has been offered.

GRF has so far been isolated and purified as peptides being composed of 44, 40, 37 and 29 amino acids, and all of them have been confirmed to have growth hormone releasing activity. These peptides are expected to be administered temporarily or for a long period for the diagnosis or medical treatment in clinical medicine, both of human medicine and veterinary medicine.

However, GRF is rather unstable and hardly preservable in a solution. It is desirable for a pharmaceutical preparation to keep GRF in the form of a lyophilized preparation. Even the lyophilized preparation is not satisfactory yet, showing significant reduction in the titer when preserved at room temperature over a long period or exposed to heating, humidification or lighting. One of the causes is that methionine at position 27 of amino acids forming GRF is liable to be oxidized. Although attempts had been made to stabilize it by addition of antioxidants such as L-ascorbic acid, no lyophilized preparations with enough long-time stability could be obtained yet.

After strenuous efforts to dissolve the difficulty, the present inventors have found that human serum albumin or glycine greatly facilitates an improvement in stability of GRF and a preparation in practical use is obtained. This invention is based on this finding.

Any GRF may be used in the present preparation as long as it is peptide having growth hormone releasing activity. For example, it is no matter whether the number of amino acids may be 44, 40, 37 or 29. The GRF may be in a mixture thereof.

There is no limitation to the dosage form of the present GRF preparation. That is, it may be a solution or a solid preparation. A lyophilized preparation is preferable as a pharmaceutical preparation with long-time stability. More preference is that nitrogen gas is introduced into an ampoule of the lyophilized preparation. The lyophilized preparation of GRF concerned with this invention has a remarkable stability compared to preparations containing other additive. The present lyophilized preparation is also able to be freely dissolved at the time of use by addition of some appropriate dissolving solution such as distilled water for injection or physiological saline solution. Conveniently, the dissolution above may be conducted just before use for injection.

There is no critical limitation to an amount of human serum albumin or glycine to be added, but it will be appropriate to add 100 μg to 30 mg per 100 μg GRF.

In order to make the preparation more stable, it is preferred to add buffer. Any buffer may be used, which are familiar to the medical preparations, for instance, acetate, phosphate or citrate. In the case of liquid preparation such as an injectable preparation or an intranasal drug, the amount of the buffer to be added may usually be enough to keep the preparation's pH at 2 to 7, preferably 2.5 to 5, taking the physical and chemical stability of GRF into consideration. In the case of a lyophilized preparation, the amount of addition of the buffer may be such that the pH of the preparation is kept within the same range as above, after re-dissolution. The present preparation may further contain additives such as an isotonizer, a soothing agent and an excipient.

The present preparation is preferred by any method familiar to the skilled in the art. For example, in the case of an injectable preparation, human serum albumin or glycine is just added to distilled water for injection or to appropriate buffer, GRF is added thereto until it is dissolved and then the solution is subjected to filtration for sterilization. The solution thus obtained is further subjected to lyophilization in a conventional manner. If necessary, nitrogen gas is introduced into an ampule to obtain an injection preparation lyophilized and kept in nitrogen atmosphere.

This invention is explained in more detail by examples.

EXPERIMENT 1

An experiment was conducted in order to confirm the stabilizing effect of this invention. Various stabilizers were dissolved in aqueous solutions containing GRF (1-44) and lyophilized and then nitrogen gas was introduced. Then examination was made for the items listed in Table 1. It was found that the lyophilized preparation to which human serum albumin or glycine had been added showed a remarkable stability compared to other stabilizers.

TABLE 1

Comparison of stabilizers [GRF (1-44)]

| Storage conditions | Item | Human serum albumin (1 mg) | Glycine (4 mg) | D-mannitol (10 mg) | L-ascorbic acid (1 mg) |
|---|---|---|---|---|---|
| Initial | Description of solution | Colorless & clear | Colorless & clear | Colorless & clear | Colorless & clear |
|  | Content (%) | 100 | 100 | 100 | 100 |
| 50° C. for 15 days | Description of solution | Colorless & clear | Colorless & clear | Colorless & clear | Pale Yellow |
|  | Content (%) | 99 | 81 | 52 | 42 |

Note:
Figures in parentheses indicate the amount of stabilizer added per 100 μg GRF (1-44). GRF content was assayed by high performance liquid chromatography.

EXPERIMENT 2

An experiment was conducted in order to confirm the stabilizing effect of this invention. Various stabilizers were dissolved in phosphate buffer solutions containing GRF (1-29). These solutions were lyophilized and nitrogen gas was introduced. Then examination was made for the items listed in Table 2. It was found that the stability of GRF (1-29) was increased by the addition of human serum albumin or glycine.

On the contrary, the lyophilized preparation added cysteine or sodium thiosulfate showed decrease of potency and appearance change.

TABLE 2

Comparison of stabilizers [GRF (1-29)]

| Storage conditions | Item | Stabilizer | | | | |
|---|---|---|---|---|---|---|
| | | No addition | Human serum albumin (1 mg) | Glycine (10 mg) | Human serum albumin (1 mg) Cysteine (2 mg) | Human serum albumin (1 mg) Sodium thiosulfate (2 mg) |
| Initial | Description of solution | Colorless & clear | Colorless & clear | Colorless & clear | Colorless & clear | Colorless & clear |
| | pH | 5.3 | 5.4 | 5.3 | 2.8 | 5.0 |
| | Content (%) | 100 | 100 | 100 | 100 | 100 |
| 50° C. for 15 days | Description of solution | Colorless & clear | Colorless & clear | Colorless & clear | Colorless & clear | Opalescence |
| | Content (%) | 65 | 95 | 89 | 22 | 13 |

Note:
Figures in parentheses indicate the amount of stabilizer added per 100 μg GRF (1-29). GRF content was assayed by high performance liquid chromatography.

Examples are presented below. It is needless to say that this invention is not limited thereto.

EXAMPLE 1

200 mg of human serum albumin was added to 10 ml of acetic acid—sodium acetate buffer at pH 5, and then 10 mg of GRF (1-44) was dissolved. After this solution was filtered through a sterile filter and dispensed as 100 μl of solution per 4 ml glass vial and lyophilized. After lyophilization, the vial was closed under nitrogen atmosphere. A stable lyophilized preparation for injection was thus obtained.

EXAMPLE 2

100 mg of human serum albumin was added to 50 ml of phosphoric—citric buffer at pH 3, and then 10 mg of GRF (1-44) was dissolved. After this solution was filtered through a sterile filter and dispensed as 500 μl of solution per 4 ml glass vial and lyophilized. After lyophilization, the vial was closed under nitrogen atmosphere. A stable lyophilized preparation for injection was thus obtained.

EXAMPLE 3

400 mg of glycine was dissolved in 50 ml of distilled water for injection, and then 10 mg of GRF (1-44) was dissolved. After this solution was filtered through a sterile filter and dispensed as 500 μl of solution per 4 ml glass vial and lyophilized. After lyophilization, the vial was closed under nitrogen atmosphere. A stable lyophilized preparation for injection was thus obtained.

EXAMPLE 4

4 mg of GRF (1-29) was dissolved in 20 ml of 1/10 M phosphate buffer at pH 5, and then 40 mg of human serum albumin was added. After this solution was filtered through a sterile filter and dispensed as 500 μl of solution per 4 ml glass vial and lyophilized.

After lyophilization, the vial was closed under nitrogen atmosphere. A stable lyophilized preparation for injection was thus obtained.

EXAMPLE 5

4 mg of GRF (1-29) was dissolved in 20 ml of 1/10 M phosphate buffer at pH 5, and then 40 mg of human serum albumin and 280 mg of sodium chloride were added. After this solution was filtered through a sterile filter and dispensed as 500 μl of solution per 4 ml glass vial and lyophilized.

After lyophilization, the vial was closed under nitrogen atmosphere. A stable lyophilized preparation for injection was thus obtained.

EXAMPLE 6

4 mg of GRF (1-29) was dissolved in 20 ml of 1/10 M phosphate buffer at pH 5, and then 40 mg of human serum albumin and 360 mg of sodium chloride were added. After this solution was filtered through a sterile filter and dispensed as 500 μl of solution per 4 ml glass vial and lyophilized.

After lyophilization, the vial was closed under nitrogen atmosphere. A stable lyophilized preparation for injection was thus obtained.

EXAMPLE 7

4 mg of GRF (1-29) was dissolved in 20 ml of 1/10 M phosphate buffer at pH 5, and then 40 mg of human serum albumin and 400 mg of mannitol were added. After this solution was filtered through a sterile filter and dispensed as 500 μl of solution per 4 ml glass vial and lyophilized.

After lyophilization, the vial was closed under nitrogen atmosphere. A stable lyophilized preparation for injection was thus obtained.

EXAMPLE 8

20 mg of GRF (1-29) was dissolved in 20 ml of 1/10 M phosphate buffer at pH 5, and then 40 mg of human serum albumin was added. After this solution was filtered through a sterile filter and dispensed as 500 μl of solution per 4 ml glass vial and lyophilized.

After lyophilization, the vial was closed under nitrogen atmosphere. A stable lyophilized preparation for injection was thus obtained.

EXAMPLE 9

20 mg of GRF (1-29) was dissolved in 20 ml of 1/10 M phosphate buffer at pH 5, and then 200 mg of human serum albumin and 280 mg of sodium chloride were added. After this solution was filtered through a sterile filter and dispensed as 500 μl of solution per 4 ml glass vial and lyophilized.

After lyophilization, the vial was closed under nitrogen atmosphere. A stable lyophilized preparation for injection was thus obtained.

EXAMPLE 10

20 mg of GRF (1-29) was dissolved in 100 ml of 1/10 M phosphate buffer at pH 5, and then 200 mg of human serum albumin and 1.4 g of sodium chloride were added. After this solution was filtered through a sterile filter and dispensed as 2.5 ml of solution per 4 ml glass vial and lyophilized.

After lyophilization, the vial was closed under nitrogen atmosphere. A stable lyophilized preparation for injection was thus obtained.

We claim:

1. A growth hormone releasing composition consisting essentially of human growth hormone releasing factor (GRF) and a stability enhancing amount of a stabilizing agent selected from the group consisting of human serum albumin or glycine wherein said GRF has the amino acid sequence H—Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Met—Ser—Arg—Gln—Gln—Gly—Glu—Ser—Asn—Gln—Glu—Arg—Gly—Ala—Arg—Ala—Arg—Leu—NH$_2$ or the amino acid sequence H—Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Iln—Met—Ser—Arg—NH$_2$.

2. A composition as in claim 1 further comprising a buffer selected from the group consisting of acetate, citrate and phosphate buffers wherein the amount of said buffer is an amount sufficient to maintain the pH of the composition at pH 2 to 6.

3. A composition as in claim 1 wherein the amount of glycine or human serum albumin comprises 100 micrograms to 30 milligrams, per 100 micrograms of growth hormone releasing factor.

4. A composition as in claim 1 wherein said composition is lyophilized.

5. A composition as in claim 4 wherein said composition is maintained under a nitrogen gas atmosphere.

6. A composition as in claim 1 further comprising one of the group consisting of a pharmaceutically acceptable carrier, an isotonizer and a soothing agent.

7. A process enhancing the stability of a growth hormone releasing factor (GRF) composition consisting essentially of adding a stability enhancing amount of a stabilizing agent selected from the group consisting of human serum albumin and glycine to GRF wherein said GRF has the amino acid sequence H—Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Met—Ser—Arg—Gln—Gln—Gly—Glu—Ser—Asn—Gln—Glu—Arg—Gly—Ala—Arg—Ala—Arg—Leu—NH$_2$ or the amino acid sequence H—Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Met—Ser—Arg—NH$_2$.

8. A process as in claim 7 further comprising a buffer selected from the group consisting of acetate, citrate and phosphate buffers wherein the amount of said buffer is an amount sufficient to maintain the pH of the composition at pH 2 to 6.

9. A process in claim 7 wherein the amount of glycine or human serum comprises 100 micrograms to 30 milligrams per 100 micrograms of growth hormone releasing factor.

10. A process as in claim 7 wherein said composition is lyophilized.

11. A process as in claim 10 wherein said composition is maintained under a nitrogen gas atmosphere.

12. A process as in claim 7 further comprising one of the group consisting of a pharmaceutically acceptable carrier, an isotonize and a soothing agent.

* * * * *